United States Patent [19]

Kelman

[11] 4,404,694

[45] Sep. 20, 1983

[54] INTRAOCULAR LENS

[76] Inventor: Charles D. Kelman, 269-70 Grand Central Pkwy., Floral Park, N.Y. 11005

[21] Appl. No.: 359,508

[22] Filed: Mar. 18, 1982

[51] Int. Cl.³ .............................. A61F 1/16; A61F 1/24
[52] U.S. Cl. .......................................................... 3/13
[58] Field of Search .......................................... 3/13, 1

[56] References Cited

U.S. PATENT DOCUMENTS

| | | | |
|---|---|---|---|
| 3,922,728 | 12/1975 | Krasnov | 3/13 |
| 3,986,214 | 10/1976 | Krasnov | 3/13 |
| 4,092,743 | 6/1978 | Kelman | 3/13 |
| 4,159,546 | 7/1979 | Shearing | 3/13 |
| 4,174,543 | 11/1979 | Kelman | 3/13 |
| 4,242,760 | 1/1981 | Rainin | 3/13 |
| 4,253,200 | 3/1981 | Kelman | 3/13 |
| 4,254,510 | 3/1981 | Tennant | 3/13 |
| 4,298,994 | 11/1981 | Clayman | 3/13 |

*Primary Examiner*—Ronald L. Frinks
*Attorney, Agent, or Firm*—Henry Sternberg

[57] ABSTRACT

An intraocular lens structure utilizing a lens which may be placed adjacent the posterior side of the iris and adapted for covering at least a portion of the pupil. The structure includes a first position fixation element connected to the lens body which extends away from the same to the periphery of the iris for engagement in the posterior chamber. A second position fixation element connected to the lens body includes a first portion which extends away from the lens body, a second portion intended for passing through an opening in the iris wall into the anterior chamber and an end portion which extends to the periphery of the iris in the anterior chamber and engages the same. The end portions of the first and second position fixation elements are sprung between the anterior chamber angle on the one hand and the capsular sulcus on the other hand.

14 Claims, 3 Drawing Figures

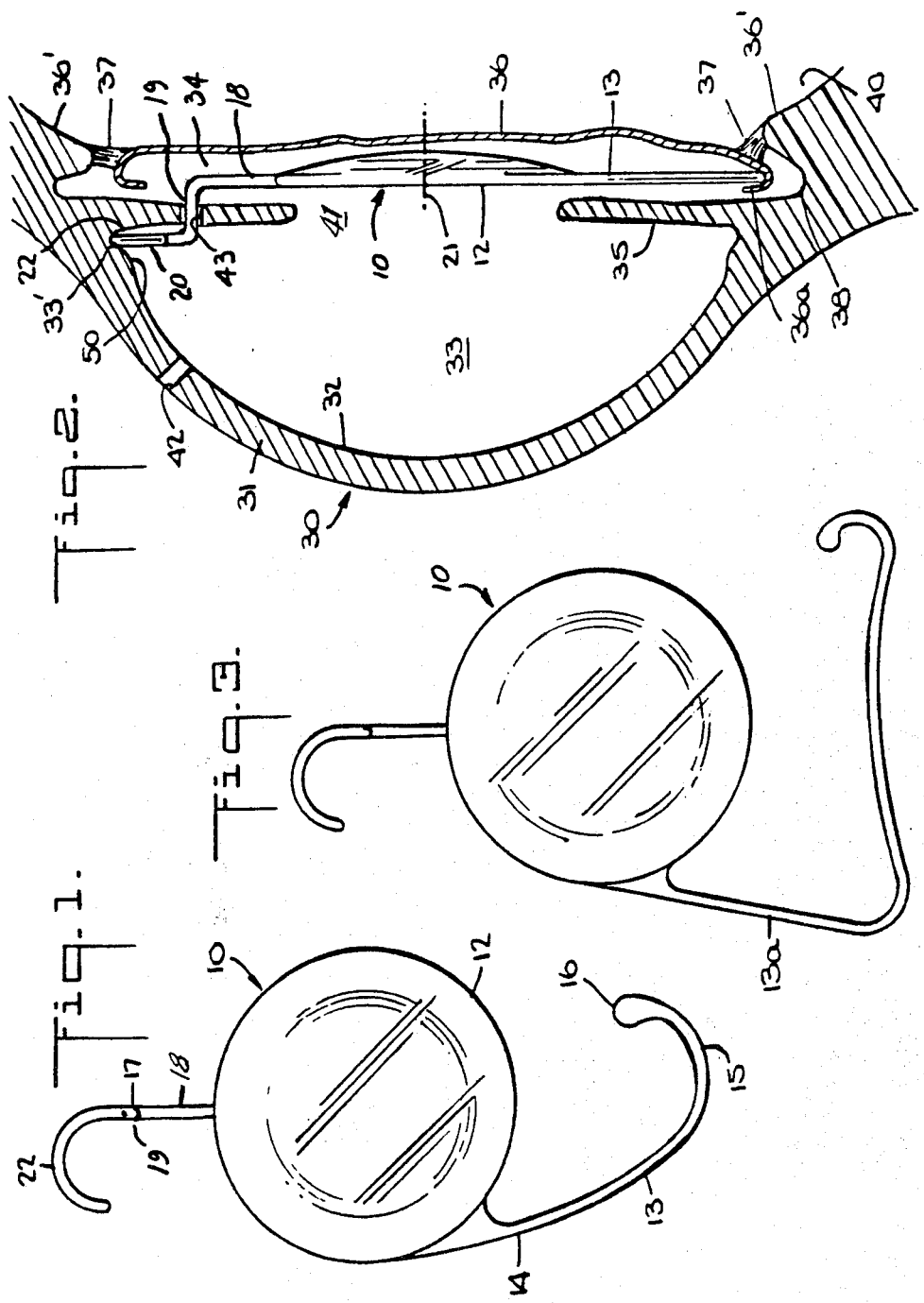

INTRAOCULAR LENS

BACKGROUND OF THE INVENTION

The present invention relates to an intraocular lens structure designed to be seated partly in the anterior and partly in the posterior chamber of the eye after the removal of a natural lens as a result of a cataract condition.

It has been found that the insertion of an intraocular lens is by far the best solution to correcting vision after cataract surgery. The proper placement of an intraocular lens always involves the risk of damage to the eye during the insertion process as well as at a later time if the intraocular lens dislocates or for some other reason must be removed and/or replaced.

Lenses are known which permit posterior chamber fixation. However, with the known posterior chamber lenses, suitable posterior fixation of the lenses is difficult to predict since visibility of the fixation of the upper foot is totally impossible. The ciliary sulcus region at the upper portion of the eye is totally hidden by the iris and is, therefore, not visible to the surgeon during the implant procedure. Consequently the upper foot is often inadvertently seated in the ciliary sulcus between the capsule and the iris rather than in the capsule itself. Should that occur, removal of the lens, should such be indicated at some later date, may be extremely difficult and sometimes dangerous, in part because the field is not visible to the surgeon but also because adhesion in the ciliary sulcus is substantially greater than in the capsule.

There is a need for a lens which may be easily positioned in the posterior chamber of the eye, which offers a suitable means of support, and which will not result in substantial damage to the eye during removal of the lens at a later date should such removal be indicated.

While it is feasible to seat the bottom leg in the capsule, since the bottom region of the posterior chamber, at the periphery of the iris, is substantially more visible to the surgeon than the aforesaid upper region, it is highly desirable to fixate the upper leg in the anterior chamber angle rather than risk inadvertent fixation thereof in the ciliary sulcus. In the anterior chamber location the upper leg is not only fully exposed to the view of the surgeon both during implantation and later removal but substantially less adhesion will result.

According to the present invention, therefore, the upper leg has a portion extending through the iridectomy from the posterior side of the iris to the anterior side thereof, so that the free end portion of the upper leg can be fixated at the periphery of the iris on the anterior chamber side thereof. There is the further advantage according to this invention with respect to my earlier posterior chamber lens described and claimed in my U.S. patent application Ser. No. 244,930 filed Mar. 18, 1981, now U.S. Pat. No. 4,340,979, that in accordance with the instant invention no portion of the lens extends through the pupil. This eliminates the possibility of any vision distortion resulting from lens constructions in which the top leg of the lens is connected to the optic at a point close to the optic axis while at the same time avoiding the possibility of deformation of the pupil as a result of the portion of the iris which defines the pupil contacting the upper leg in those constructions in which such upper leg connects closer to the periphery of the optic and at such time as the pupil is constricted. The present invention eliminates the possibility of these risks which exist with lenses in which one of the legs extends through the pupil.

SUMMARY OF THE INVENTION

In accordance with the invention, an intraocular lens suitable for use as an artificial lens implant comprises a medial, light-focusing, lens body intended to be positioned adjacent the pupil on one side of the iris and a pair of position fixation elements connected with the lens body. One of the position fixation elements has a first portion contiguous to and extending generally laterally outwardly from a first region of the periphery of said lens body and intended to extend to and seat adjacent the periphery of the iris on the aforesaid one side thereof. The other of the position fixation elements has a first portion extending generally laterally outwardly from a second region of the periphery of the lens body spaced from the aforesaid first region and in a direction generally opposite to that of the aforesaid first portion of the aforesaid one position fixation element. The other position fixation element has a second portion extending from the first portion thereof and intended to extend through an opening in the iris from the aforesaid one side of the iris to the other side of the iris and a third portion connected to the second portion and intended to extend to and seat adjacent the periphery of the iris on the aforesaid other side thereof.

Also in accordance with the invention, an intraocular lens suitable for use as an artificial lens implant having an optical zone positioned posteriorly of the iris comprises a medial, light-focusing lens body and at least a pair of position fixation elements connected with the lens body. At least one of the pair of position fixation elements has a first portion contiguous to and extending generally laterally outwardly from a first region of the periphery of the lens body and intended for seating in the sulcus of the posterior chamber capsule. The other of the pair of position fixation elements has a first portion extending generally laterally outwardly from a second region of the periphery of the lens body spaced from the first region and in a direction generally opposite to that of the first portion of the aforesaid one position fixation element. The other position fixation element has a second portion extending from the first portion thereof and intended to extend through an opening in the iris from the posterior side of the iris to the anterior side of the iris. The other position fixation element has a third portion connected to the second portion and intended to extend to the periphery of the iris for sealing in the anterior chamber angle of the eye.

Also in accordance with the invention, the method of inserting the optical zone of an intraocular lens into the posterior chamber of an eye comprises inserting a first position fixation element, extending generally laterally outwardly from the lens body, through the pupil into the sulcus of the posterior chamber capsule. The method also includes inserting a second position fixation element, extending outwardly from the lens body, through an opening in the iris into the anterior chamber angle of the eye.

Means for urging engagement of the first and second position fixation elements to the periphery of the iris may take the form of a spring mechanism and the like. It has been found that simply forming at least a portion of the first and/or second position fixation elements of resilient material produces a spring-like effect. In addition, each position fixation element may be an elongated member having a curved end portion with a blunted tip to prevent damage to the eye tissue during and after insertion of the lens structure.

It is an object of the present invention to provide an intraocular lens structure which may be employed to correct aphakia after cataract surgery accomplished by extra capsular cataract extraction.

It is yet another object of the present invention to provide an intraocular lens structure which may be inserted into the posterior chamber of the eye in such a manner that if removal becomes desirable the lens structure may be removed without substantial injury to the tissues in which the lens structure is seated.

It is a further object of the present invention to provide an intraocular lens structure which may be more easily inserted by the less experienced surgeon into the posterior chamber of the eye.

It is a still further object of the present invention to provide an intraocular lens structure, and method for inserting the same, for which the surgeon is able to visually guide at least one means of fixation of the optical zone and to stabilize the lens structure upon insertion thereof in the posterior chamber of the eye.

It is a concomitant object of the invention to provide an intraocular lens structure for positioning in the posterior chamber of the eye and which may be readily removed therefrom.

For a better understanding of the present invention, together with other and furter objects thereof, reference is made to the following description taken in connection with the accompanying drawings, and its scope will be pointed out in the appended claims.

BRIEF DESCRIPTION OF THE DRAWINGS

FIG. 1 is a plan view of an embodiment of the present invention intended for fixation partly in the posterior and partly in the anterior chamber of the eye.

FIG. 2 is a side elevational view of the intraocular lens structure of FIG. 1 fixed within an eye, shown in section.

FIG. 3 is a plan view of another embodiment of the present invention intended for fixation partly in the posterior and partly in the anterior chamber of an eye.

DESCRIPTION OF THE PREFERRED EMBODIMENTS

With reference to the drawings the invention as a whole is depicted on the figures illustrated thereupon and denoted by reference character 10. The intraocular lens structure 10 includes as one of its elements a medial, light-focusing lens body or optical zone 12, FIG. 1. The lens body 12 may be constructed of any biologically inert and transparent material suitable for optical correction such as methylmethacrylate, quartz, ophthalmic glass, and other materials known in the art.

At least a pair of position fixation elements 13, 17 are connected with the lens body 12. First position fixation element 13 has a first portion 14 contiguous to and extending generally laterally outwardly from a first region of the periphery of the lens body 12. First and second position fixation elements 13, 17 may be molded integrally with lens body 12 or connected by an adhesive, ultrasonic welding, fusion, or any other connection method known in the art. As may be seen from FIG. 1, first position fixation element 13 is an elongated member having a relatively straight portion 14 and a curved end portion 15. In other words, straight portion 14 connects to lens body 12 at the proximal end and to curved portion 15 at the distal end thereof. A knob 16 is fixed to the terminal portion 15 to prevent damage to human tissue within the eye. It should be noted that first position fixation element 13 is constructed of biologically inert and nonabsorbative material such as methylmethacrylate, polypropylene, platinum, and the like. The present embodiment anticipates that first element 13 is resilient or springy such that it will return to the position shown in FIG. 1 after compression or extension away from the illustrated configuration.

As seen in FIG. 2 lens structure 10 embraces a second position fixation element 17 as a necessary element thereof. Second element 17 includes a first portion 18 extending generally laterally outwardly from a second region of the periphery of the lens body 12 spaced from the first region and in a direction generally opposite to that of the first position fixation element 13. The second position fixation element 17 has a second portion 19 extending from the first portion 18 generally axially from the lens body, that is, generally parallel to the optical axis of the lens body and extending through an opening in the iris such as an iridectomy from one side of the iris to the other side of the iris. Second element 17 has a third portion 20 connected to the second portion 19 for extending to the periphery of the iris for seating in the anterior chamber angle 33' of the eye in the vicinity of the scleral spur 50.

The first portion 18 of the second position fixation element 17 has a length of, for example, three millimeters. The second portion 19 of the second position fixation element 17 preferably extends at substantially a right angle from the first portion thereof. The third portion 20 preferably extends at substantially a right angle from the second portion 19 and substantially perpendicular to the optical axis 21 of the lens body.

The second position fixation element 17 has a third portion 20 extending substantially parallel to the plane of the lens body and has a curved end portion 22 for seating in the anterior chamber angle 33' of the eye in the vicinity of the scleral spur 50. The distance between the plane substantially containing the curved end portion 22 and a plane perpendicular to the optical axis and containing the most anterior surface of the lens body is, for example, approximately one millimeter. The seating portion 22 is located in a plane perpendicular to the optical axis of the lens body.

The second position fixation element 17 may be made of the same material as the first position fixation element 13 and preferably is resilient or springy such that it will return to the position shown in FIG. 1 after compression or extension away from the illustrated configuration.

Lens structure 10 is intended for insertion and fixation within an eye 30, after cataract removal by extra capsular surgical procedure. Eye 30 includes a cornea 31 having an endothelial layer 32. Anterior chamber 33 and posterior chamber 34 are defined by the position of iris 35. FIG. 2 shows eye 30 after an extra capsular surgical procedure in which, after the natural lens has been removed, a relatively flattened posterior capsule membrane 36, as well as a small part of anterior capsule 36a remains. The natural lens is normally connected to the ciliary body 36' by a plurality of zonules 37. Ciliary sulcus 38 of the posterior chamber is located between the sulcus of the capsule 36 and the iris 35. As used in this specification and in the claims, the term "adjacent the periphery of the iris", referring to seating, includes seating in the anterior chamber angle of the eye in the vicinity of the scleral spur 50, seating in the sulcus of the capsule 36, 36a, and seating in the ciliary sulcus 38.

As shown in FIG. 2, lens structure 10 may be placed in posterior chamber 34 through pupil 41, which may be chemically dilated. Initially, lens structure 10 is slipped through an opening 42 of cornea 31 above the end of endothelial layer 32 which aligns with pupil 41. A pair of tweezers is employed to stabilize and to steer optical zone 12 and first element 13 through pupil 41 and to place first element 13 into seating engagement with the sulcus of capsule 36, 36a. Second element 17 is at this time also in the posterior chamber, having been passed through the pupil together with optical zone 12. Second element 17 is then passed through the opening, or iridectomy 43 in the iris, from the posterior side of the iris to the anterior side thereof and seated in the anterior chamber angle 33'. The engagement of element 17 with the iris, as well as the posterior capsule 36 prevent the lens from falling backward into the vitreous cavity 40. Curved portion 15 of first element 13 fits within the sulcus of the capsule 36, 36a at the periphery of the iris serving as a means for primary support of optical zone 12.

Second element 17 extends through the opening in the iris such that end portion 22 seats in the anterior chamber angle 33' to offer a positive means of secondary support for lens body 12 of lens structure 10.

FIG. 3 depicts another embodiment of the present invention wherein a resilient first position fixation element 13a has a first portion extending generally laterally from the lens body and a second portion extending from the end of the first portion generally transversely thereto and at least partly peripherally of the lens body to provide two points of support for the lens in the sulcus of the capsule 36. The remainder of the FIG. 3 lens structure is similar to the FIG. 1 structure.

From the foregoing description it will be apparent that a lens constructed in accordance with the invention has the advantage that its lens body may be readily positioned in the posterior chamber and yet have one of its position fixation elements seated in the anterior chamber angle where it can be seen both for implantation and for subsequent surgical removal, if necessary, thus facilitating both the implantation and any subsequent removal. Further, surgeons have nearly twenty years of experience with seating position fixation elements in the anterior chamber angle while they have only three or four years experience with seating position fixation elements in the posterior chamber. Thus seating one of the position fixation elements in the anterior chamber facilitates the surgical procedure but even more importantly provides a degree of confidence regarding the safety and efficiency of the procedure and of the resulting implant.

While there have been described what are at present considered to be the preferred embodiments of this invention, it will be obvious to those skilled in the art that various changes and modifications may be made therein whithout departing from the invention, and it is, therefore, aimed to cover all such changes and modifications as fall within the true spirit and scope of the invention.

What is claimed is:

1. An intraocular lens suitable for use as an artificial lens implant, the lens comprising:
 a medial, light-focusing, lens body intended to be positioned adjacent the pupil on one side of the iris; and
 at least a pair of position fixation elements connected with said lens body;
 one of said position fixation elements having a first portion contiguous to and extending generally laterally outwardly from a first region of the periphery of said lens body and intended to extend to and seat adjacent the periphery of the iris on said one side thereof;
 the other of said position fixation elements having a first portion extending generally laterally outwardly from a second region of the periphery of said lens body spaced from said first region and in a direction generally opposite that of said first portion of said one position fixation element, a second portion extending from said last-mentioned first portion and intended to extend through an opening in the iris from said one side of the iris to the other side of the iris and a third portion connected to said second portion and intended to extend to and seat adjacent the periphery of the iris on said other side thereof.

2. The intraocular lens as claimed in claim 1 wherein said first portion of said other of said pair of position fixation elements extends in generally radial direction from the second region of the periphery of said lens body.

3. The intraocular lens as claimed in claim 1 wherein said first and third portions of said other of said pair of position fixation elements extend in generally radial direction from said lens body and said second portion of said other position fixation element extends in generally axial direction with respect to said lens body.

4. The intraocular lens as claimed in claim 3 wherein said third portion of said other of said pair of position fixation elements has a seating portion adapted to seat in the eye adjacent the periphery of the iris on said other side thereof, said seating portion being located in a plane perpendicular to the optical axis of the lens body and being at the distal end of said second portion of said other position fixation element.

5. The intraocular lens as claimed in claim 4 wherein the length of said second portion of said other position fixation element is sufficient to permit movement of the iris between said seating portion of said other position fixation element and said lens body.

6. The intraocular lens as claimed in claim 4, wherein said first portion of said one position fixation element has a sealing portion adapted to seat adjacent the periphery of the iris on said one side thereof, and at least one of said seating portions has a pair of contact surfaces for providing together with said other seating portion at least three-point fixation for the lens.

7. An intraocular lens suitable for use as an artificial lens implant having an optical zone positioned posteriorly of the iris, the lens comprising:
 a medial, light-focusing lens body intended to be positioned adjacent the pupil on the posterior side of the iris; and
 at least a pair of position fixation elements connected with said lens body;
 at least one of said pair of position fixation elements having a first portion contiguous to and extending generally laterally outwardly from a first region of the periphery of said lens body intended for seating in the sulcus of the posterior chamber capsule;
 the other of said pair of position fixation elements having a first portion extending generally laterally outwardly from a second region of the periphery of said lens body spaced from said first region and in a direction generally opposite to that of said first portion of said one position fixation element, a second portion extending from said last-mentioned first portion and intended to extend through an opening in the iris from the posterior chamber side of the iris to the anterior chamber side of the iris, and a third portion connected to said second portion for extending to the periphery of the iris and intended for seating in the anterior chamber angle of the eye.

8. An intraocular lens in accordance with claim 7 in which at least one of said position fixation elements is of resilient material.

9. An intraocular lens in accordance with claim 7 in which said first position fixation element has a curved end portion for seating in the sulcus of the capsule.

10. An intraocular lens in accordance with claim 7 in which said first position fixation element is shaped to provide two points of support for the lens in the sulcus of the posterior chamber of the capsule.

11. An intraocular lens in accordance with claim 7 in which said first portion of said other of said pair of position fixation elements has a length of substantially three millimeters.

12. An intraocular lens in accordance with claim 7 or claim 8 in which said second portion of said other of said pair of fixation elements extends at substantially a right angle from said first portion thereof and said third portion thereof extends at substantially a right angle from said second portion thereof and has a curved end portion for seating in the anterior chamber angle of the eye.

13. An intraocular lens in accordance with claim 12 in which the distance between a plane substantially containing said curved end portion of said other of said pair of position fixation elements and a plane perpendicular to said optical axis and containing the most anterior surface of said lens body is substantially one millimeter.

14. The method of inserting the optical zone of an intraocular lens into the posterior chamber of an eye comprising:
   inserting a first position fixation element extending generally laterally outwardly from the lens body through the pupil into the sulcus of the posterior chamber capsule; and
   inserting a second position fixation element extending outwardly from the lens body through an opening in the iris from the posterior side of the iris into the anterior chamber angle of the eye.

* * * * *